US011690571B2

(12) United States Patent
Yu et al.

(10) Patent No.: US 11,690,571 B2
(45) Date of Patent: Jul. 4, 2023

(54) WRISTBAND BIOSENSING SYSTEM, WRISTBAND BIOSENSING APPARATUS AND BIOSENSING METHOD

(71) Applicant: Industrial Technology Research Institute, Hsinchu (TW)

(72) Inventors: Cheng-Hung Yu, Taoyuan (TW); Ming-Huan Yang, Hsinchu (TW); Kuang-Ching Fan, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 519 days.

(21) Appl. No.: 16/820,678

(22) Filed: Mar. 16, 2020

(65) Prior Publication Data

US 2021/0100512 A1 Apr. 8, 2021

(30) Foreign Application Priority Data

Oct. 4, 2019 (TW) ................................ 108136086

(51) Int. Cl.
*A61B 5/00* (2006.01)
*A61B 5/0295* (2006.01)
*A61B 5/026* (2006.01)

(52) U.S. Cl.
CPC ............ *A61B 5/6843* (2013.01); *A61B 5/002* (2013.01); *A61B 5/0261* (2013.01);
(Continued)

(58) Field of Classification Search
CPC ..... A61B 5/6843; A61B 5/002; A61B 5/0261; A61B 5/0295; A61B 5/6824; A61B 5/742; A61B 2560/0214
See application file for complete search history.

(56) References Cited

U.S. PATENT DOCUMENTS 8,311,605 B2 * 11/2012 Wilder-Smith ...... A61B 5/0533
600/382
9,091,715 B2 7/2015 Alameh et al.
(Continued)

FOREIGN PATENT DOCUMENTS

CA 2379131 C * 4/2006 ......... A61B 5/02007
CN 102113884 7/2011
(Continued)

OTHER PUBLICATIONS

"Office Action of Taiwan Counterpart Application," dated Mar. 10, 2020, p. 1-p. 5.
(Continued)

*Primary Examiner* — Franklin D Balseca
(74) *Attorney, Agent, or Firm* — JCIPRNET

(57) ABSTRACT

A wristband biosensing system, a wristband biosensing apparatus, and a biological sensing method are provided. The system includes a wristband body worn on a wrist of a user, at least one physiological signal sensor, at least one deformation sensor, and a processing device coupled to the physiological signal sensor and the deformation sensor. The physiological signal sensor is disposed on the wristband body at a position corresponding to at least one sensing portion of the wrist to detect a physiological signal of each sensing portion. The deformation sensor is disposed around each physiological signal sensor to detect deformation of each sensing portion and output a deformation signal. The processing device receives the physiological signal and the deformation signal, inquires a compensation signal corresponding to the deformation signal, and corrects the physiological signal by using the compensation signal, so as to output a corrected physiological signal of each sensing portion.

15 Claims, 8 Drawing Sheets

(52) U.S. Cl.
CPC .......... *A61B 5/0295* (2013.01); *A61B 5/6824* (2013.01); *A61B 5/742* (2013.01); *A61B 2560/0214* (2013.01)

(56) References Cited

U.S. PATENT DOCUMENTS

| | | | |
|---|---|---|---|
| 9,521,868 B2 * | 12/2016 | Cobbett | A61B 5/7455 |
| 10,129,628 B2 * | 11/2018 | Wisbey | H04R 1/1041 |
| 10,285,645 B2 * | 5/2019 | Bushnell | A61B 5/681 |
| 10,758,732 B1 * | 9/2020 | Heldman | A61B 5/291 |
| 2015/0157269 A1 | 6/2015 | Lisogurski et al. | |
| 2016/0374620 A1 | 12/2016 | Lisogurski et al. | |
| 2017/0105646 A1 | 4/2017 | Bryenton et al. | |

FOREIGN PATENT DOCUMENTS

| | | | |
|---|---|---|---|
| CN | 202589508 | | 12/2012 |
| CN | 104545824 | | 4/2015 |
| CN | 107320095 | | 11/2017 |
| CN | 107536607 A | * | 1/2018 |
| CN | 105324080 | | 2/2019 |
| CN | 209003983 | | 6/2019 |
| CN | 110151130 | | 8/2019 |
| CN | 110944579 | | 3/2020 |
| TW | I596455 | | 8/2017 |
| WO | WO-2014066791 A1 * | 5/2014 | ........... A61B 5/0022 |

OTHER PUBLICATIONS

"Office Action of China Counterpart Application", dated Jan. 6, 2023, p. 1-p. 7.

* cited by examiner

WRISTBAND BIOSENSING SYSTEM, WRISTBAND BIOSENSING APPARATUS AND BIOSENSING METHOD

CROSS-REFERENCE TO RELATED APPLICATION

This application claims the priority benefit of Taiwan application serial no. 108136086, filed on Oct. 4, 2019. The entirety of the above-mentioned patent application is hereby incorporated by reference herein.

TECHNICAL FIELD

The technical field relates to a wristband biosensing system, a wristband biosensing apparatus, and a biosensing method.

BACKGROUND

Today's biosensor technologies are generally applied in form of wearable devices, and users wear smart watches, bracelets, patches, and other sensing devices on their bodies to sense users' physiological signals in a non-invasive manner. Here, the smart watch sensing device is generally worn on the back of a wrist to detect physiological signals, such as a heart rate, an electrocardiogram, etc. However, microvessels and veins are distributed on the back of the wrist, which is not conducive to optical heart rate sensing, and compared with the heart rate measured through the veins, the heart rate measured through medial wrist artery (supplying blood with a bright color and having large vessel thickness and small interference) is more accurate. Moreover, the device cannot well fit the back of the wrist, which is easily to cause artifacts caused by scattering or leakage of the sensing light, and whiles the user wearing the device is moving, the position of the sensor is prone to shift, and the blood vessels may be squeezed and deformed. All these factors reduce the accuracy of the physiological signals measured by the device or even cause distortion.

SUMMARY

In an embodiment of the disclosure, a wristband biosensing system including a wristband body, at least one physiological signal sensor, at least one deformation sensor, and a processing device is provided. The wristband body is worn on a wrist of a user. The physiological signal sensor is disposed on the wristband body at a position corresponding to at least one sensing portion of the wrist, and configured to detect a physiological signal of each sensing portion. The deformation sensor is disposed around each physiological signal sensor, and configured to detect deformation of each sensing portion and output a deformation signal. The processing device is coupled to the physiological signal sensor and the deformation sensor, and configured to receive the physiological signal and the deformation signal, inquire a compensation signal corresponding to the deformation signal, and correct the physiological signal by using the compensation signal, so as to output a corrected physiological signal of each sensing portion.

In an embodiment of the disclosure, a biosensing method adapted to a biosensing apparatus worn on a wrist of a user is provided, and the biosensing apparatus includes at least one physiological signal sensor, at least one deformation sensor, and a processing device, and the biosensing method includes: respectively detecting a physiological signal of at least one sensing portion of the wrist by using the physiological signal sensor by the processing device; detecting deformation of each sensing portion and inquiring a compensation signal corresponding to the deformation by using the deformation sensor by the processing device, and correcting the physiological signal by using the compensation signal by the processing device, so as to output a corrected physiological signal of each sensing portion.

In an embodiment of the disclosure, a wristband biosensing apparatus including a connection device, a wristband body, at least one physiological signal sensor, at least one deformation sensor, and a processing device is provided. The connection device is connected to a host. The wristband body is worn on a wrist of a user. The at least one physiological signal sensor is disposed on the wristband body at a position corresponding to at least one sensing portion of the wrist, and configured to detect a physiological signal of each sensing portion. The at least one deformation sensor is disposed around each physiological signal sensor, and configured to detect deformation of each sensing portion and output a deformation signal. The processing device is coupled to the physiological signal sensor and the deformation sensor, and configured to receive the physiological signal and the deformation signal, inquire a compensation signal corresponding to the deformation signal, and correct the physiological signal by using the compensation signal, so as to output a corrected physiological signal of each sensing portion to the host.

To make the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
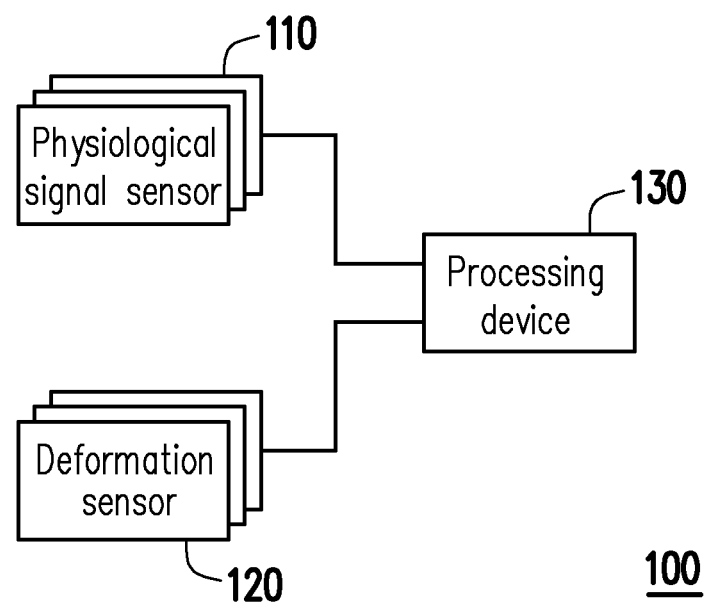
FIG. 1 is a block diagram of a wristband biosensing system according to an exemplary embodiment of the disclosure.

FIG. 1 is a block diagram of a wristband biosensing system according to an exemplary embodiment of the disclosure. Referring to FIG. 1, the wristband biosensing system 100 is adapted to a smart watch sensing device, a smart bracelet sensing device or various wristband sensing device, which is not limited by the disclosure.

The wristband biosensing system 100 includes at least one physiological signal sensor 110, at least one deformation sensor 120 and a processing device 130, where the number of the physiological signal sensors 110 and the number of the deformation sensors 120 may be adjusted according to an actual requirement (the more the numbers are, the higher the accuracy is), which is not limited by the disclosure.

In an embodiment, the physiological signal sensors 110 is, for example, disposed on a wrist body (not shown) adapted to be worn on a wrist of a user, and configured to detect one or a plurality of physiological signals of the user's wrist. The physiological signal sensor 110 may be disposed on the wristband body at a position corresponding to at least one sensing portion of the wrist to detect the physiological signal of each sensing portion.

According to a design requirement, the "physiological signal" of the embodiment may be a body temperature, a blood pressure, a pulse, a heartbeat, an electromyography (EMG) or other physiological signals, and the physiological signal sensor 110 may be a sensor adapted to detect the physiological signal, such as a Photoplethysmography Sensor (PPG sensor), etc., which is not limited by the disclosure.

The deformation sensor 120 may be disposed around each physiological signal sensor 110, and configured to detect deformation of each sensing portion and output a deformation signal. When the wrist of the user rotates or bends, each sensing portion may be deformed (i.e. muscle and skin of the wrist are deformed). Now, the deformation of each sensing portion may affect the physiological signals detected by the physiological signal sensor 110.

For example, it is assumed that the physiological signal sensor 110 is a PPG sensor, and when the user's wrist rotates or bends, a blood vessel may be bent to cause a decrease in a volume of the blood vessel, which may reduce an intensity of the signal detected by the PPG sensor. When the user's wrist does not rotate or bend, a cross section of the blood vessel is approximately round, it is assumed that a length of the blood vessel is L, and a radius of the cross section of the blood vessel is r, the volume of the blood vessel detected by the PPG sensor is then about $\pi r^2 L$. When the user's wrist rotates or bends, the cross section of the blood vessel is approximately oval, it is assumed that the length of the blood vessel is L, a half-long axis of the cross section of the blood vessel is a and a half-short axis thereof is b, and the volume of the blood vessel detected by the PPG sensor is then about $\pi ab L$. Since the volume $\pi ab L$ of the oval blood vessel is smaller than the volume $\pi r^2 L$ of the round blood vessel, i.e. bending of the wrist causes blood vessel deformation, which reduces the total volume of the blood vessel, and the signal intensity detected by the PPG sensor will decrease.

In an embodiment, the deformation sensor 120 is, for example, a capacitive deformation sensor, a resistive deformation sensor or a inductive deformation sensor, it may be configured in a manner that one deformation sensor 120 corresponds to one physiological signal sensor 110 or multiple deformation sensors 120 correspond to one physiological signal sensor 110, which is not limited by the disclosure.

The processing device 130 may be coupled to the physiological signal sensor 110 and the deformation sensor 120 to receive the physiological signal and the deformation signal, inquire a compensation signal corresponding to the deformation signal, and correct the physiological signal by using the compensation signal, so as to output a corrected physiological signal of each sensing portion. In detail, the processing device 130 may use the compensation signal to correct the physiological signal, so as to correct the influence on the physiological signal caused by the rotation or bending of the user's wrist.

Based on the above description, in an embodiment, the deformation sensor 120 may be used in advance to detect the influence on the detected physiological signal caused by the deformation of each sensing portion, and the processing device 130 establishes a mapping table to record the compensation signal required to correct the influence. Therefore, in an actual application, whenever the deformation sensor 120 detects the deformation of the sensing portion, the processing device 130 may access the pre-stored mapping table to query the compensation signal corresponding to the detected deformation.

According to a design requirement, in an embodiment, the processing device 130 may be disposed on the wristband body. In another embodiment, the processing device 130 may be disposed on a smart watch, a smart bracelet (not shown), or other electronic device that is disposed independent to the wristband body. The processing device 130 is, for example, a microprocessor, a microcontroller, an analog signal processor, a Digital Signal Processor (DSP) chip, a Field Programmable Gate Array (FPGA), an Application Specific Integrated Circuit (ASIC) or other programmable component or device, which is not limited by the disclosure.

In an embodiment, the physiological signal sensors 110 may be disposed on the wristband body in an array, and the processing device 130 may compare the physiological signal detected by each of the physiological signal sensors 110 with a referential physiological signal map of the sensing portion, so as to select the physiological signal of the sensing portion to be corrected and output.

In detail, the processing device 130 may compare the detected physiological signals with the referential physiological signal map to select the physiological signal sensors 110 close to a target portion (for example, a wrist artery), so as to correct and output the physiological signals obtained by the selected physiological signal sensors 110. According to the design requirement, the referential physiological signal map is, for example, a photo-electric volume map corresponding to the wrist artery and stored in a database, and is adapted to be accessed by the processing device 130. The database is, for example, set in a mobile device such as a smart watch, a smart bracelet, a mobile phone, etc., or is disposed in a remote server, which is not limited by the disclosure.

For example, if the physiological signal sensors 110 are PPG sensors, the processing device 130 may compare the physiological signals detected by each of the physiological signal sensors 110 with the photo-electric volume map corresponding to the wrist artery to determine the physiological signal sensors 110 located close to the wrist artery (i.e. the target portion), so as to correct and output the physiological signals detected by theses physiological signal sensors 110.

In an embodiment, the processing device 130 may select the physiological signals with the highest signal map similarity, the highest intensity or both from the detected physiological signals to serve as the physiological signals of the sensing portion to be corrected and output according to the referential physiological signal map. In detail, the processing device 130 select physiological signals that are most similar to a waveform of the referential physiological signal map, physiological signals with the highest signal intensity, or physiological signals that are most similar to the waveform of the referential physiological signal map and have the highest signal intensity, so as to correct and output the selected physiological signals.

In an embodiment, the wristband biosensing system 100 may further include a display device (not shown), and the display device is connected to the processing device 130 in a wired or wireless manner for receiving and displaying the corrected physiological signals of each of the sensing portions output by the processing device 130. For example, if the processing device 130 is disposed on a smart watch body, the deformation sensor 120 may transmit the corrected physiological signals of each of the sensing portions to the processing device 130 in a wireless manner, and the processing device 130 transmits the corrected physiological signals of each of the sensing portions to the display device for displaying in a wired manner. If the processing device 130 is disposed on the wristband body, the deformation sensor 120 may transmit the corrected physiological signals of each of the sensing portions to the processing device 130 in the wired manner, and the processing device 130 transmits the corrected physiological signals of each of the sensing portions to the display device (which is, for example, disposed on the smart watch body) for displaying in the wireless manner. Moreover, the wristband biosensing system 100 may further include a transmission module (not shown), and the transmission module may be disposed on the wristband body, the smart watch body or any device, so that the processing device 130 may transmit the corrected physiological signals of the sensing portions to a cloud server through the transmission module.

Based on the above description, the wristband biosensing system 100 may detect deformation of the wrist of the user, and use the compensation signal corresponding to the deformation to correct the physiological signal influenced by the deformation of the wrist. In this way, the wristband biosensing system 100 may eliminate the influence of the deformation of the wrist of the user on the physiological signal.

Figure 2A:
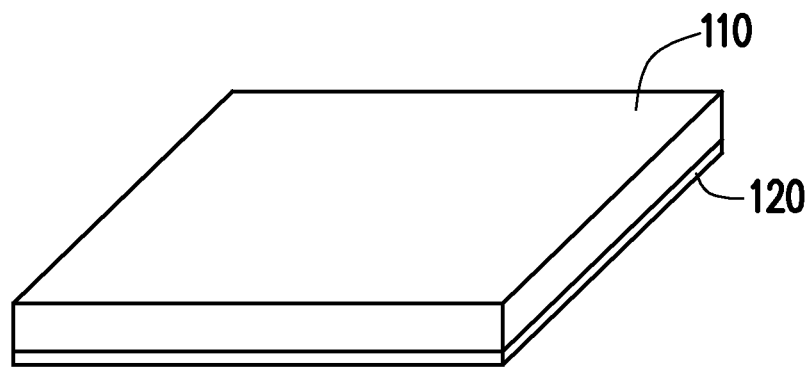
FIG. 2A to FIG. 2C are position relationship diagrams of a physiological signal sensor and a deformation sensor according to an exemplary embodiment of the disclosure.
Figure 2B:
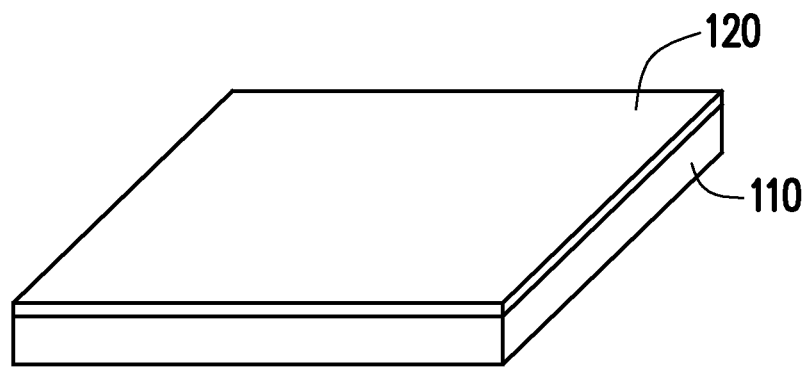
Figure 2C:
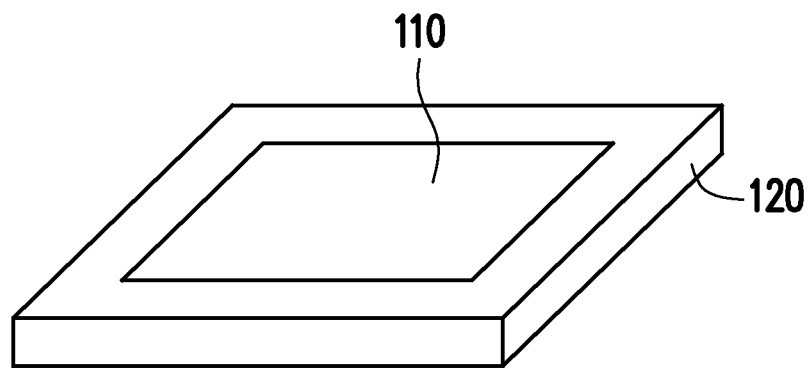

FIG. 2A to FIG. 2C are position relationship diagrams of a physiological signal sensor and a deformation sensor according to an exemplary embodiment of the disclosure. A practitioner may adjust the corresponding relationship between the physiological signal sensor and the deformation sensor according to an actual requirement and an implementation type of the deformation sensor. Referring to FIG. 2A, the deformation sensor 120 is disposed under the physiological signal sensor 110; referring to FIG. 2B, the deformation sensor 120 is disposed on top of the physiological signal sensor 110; and referring to FIG. 2C, the physiological signal sensor 110 and the deformation sensor 120 are located in a same layer, and the deformation sensor 120 is disposed around the physiological signal sensor 110. The deformation sensor 120 of FIG. 2C forms a closed loop structure around the physiological signal sensor 110, but in other embodiments, a non-closed structure may also be adopted, which is not limited by the disclosure.

Figure 3A:
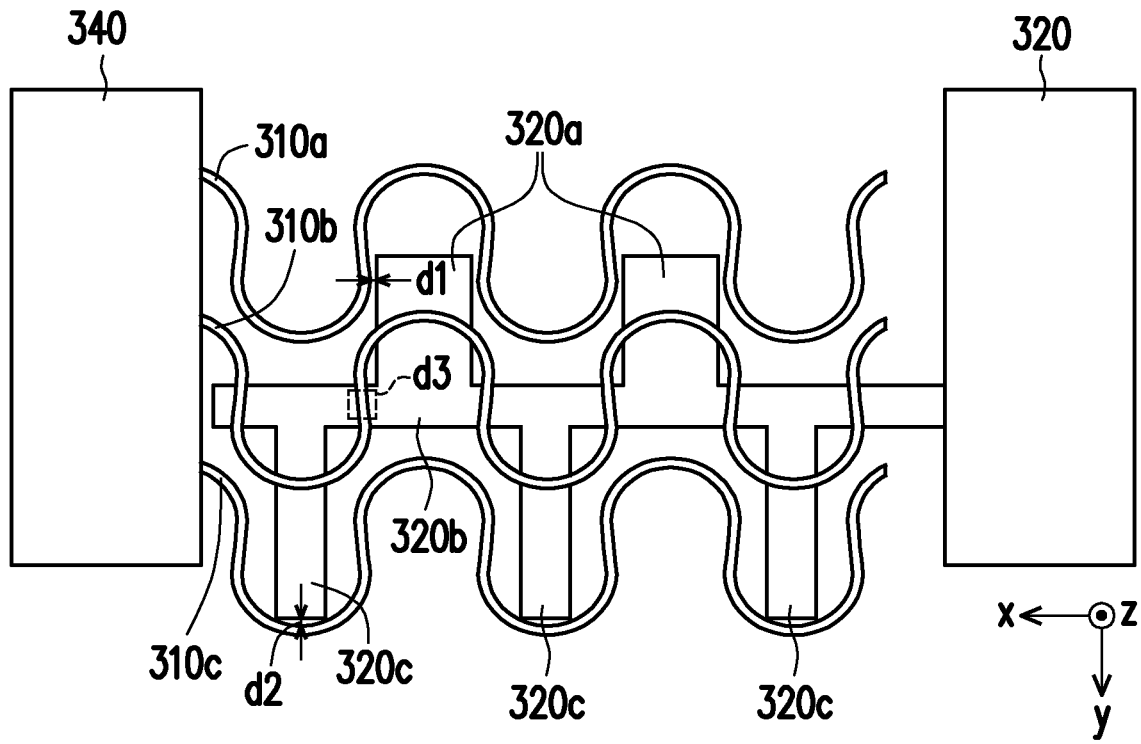
FIG. 3A to FIG. 3D are schematic diagrams of a deformation sensor according to an exemplary embodiment of the disclosure.
Figure 3B:
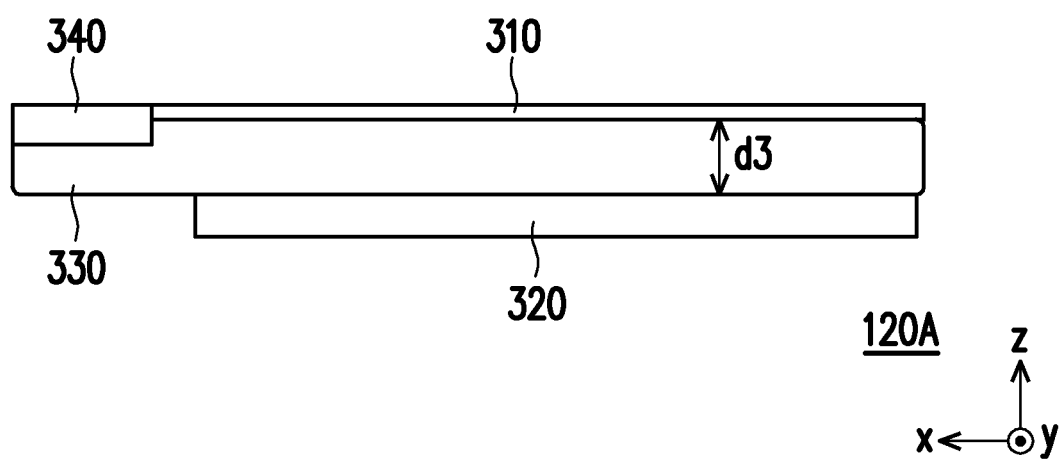
Figure 3C:
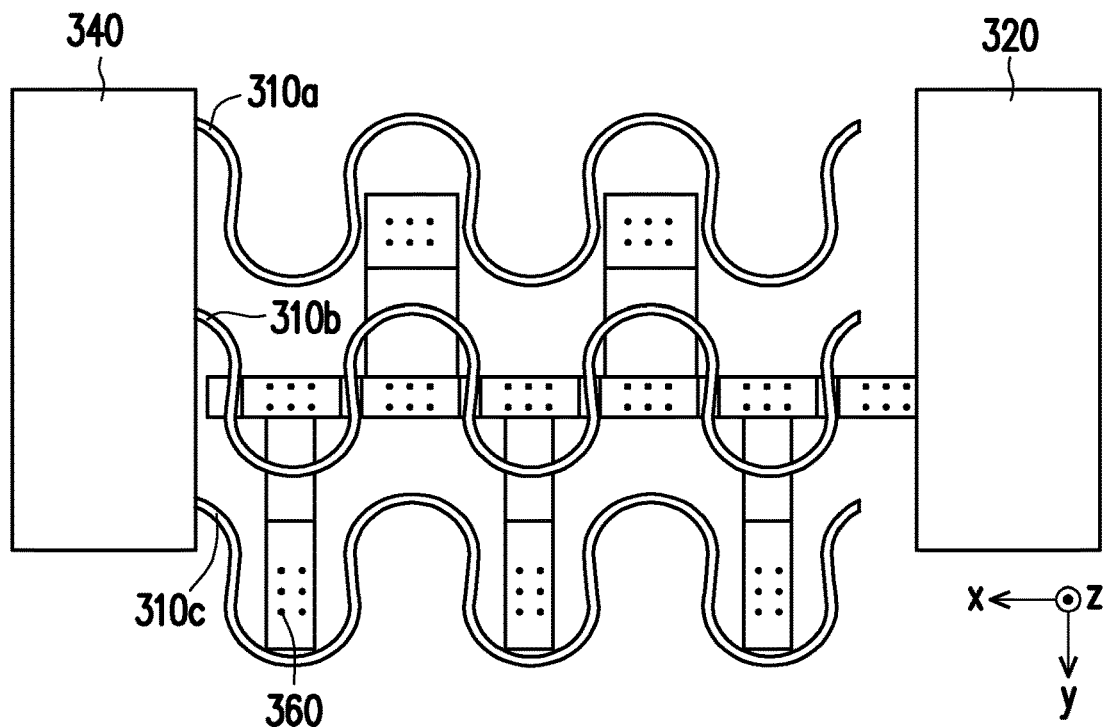
Figure 3D:
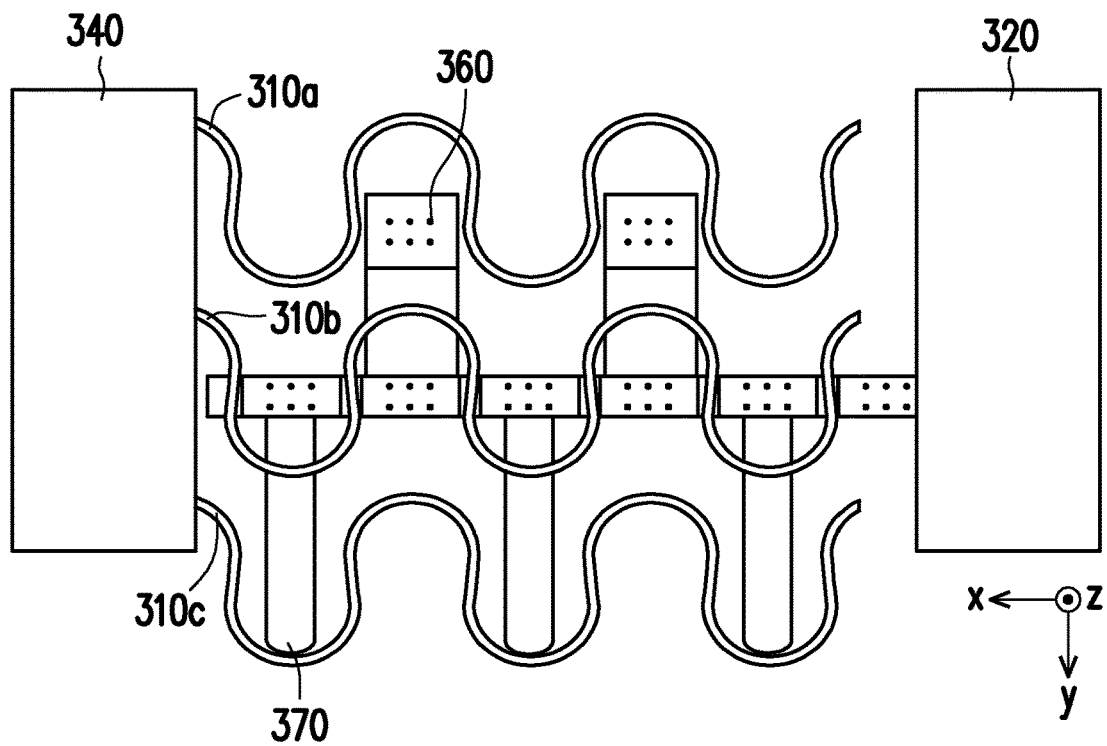

FIG. 3A to FIG. 3D are schematic diagrams of a deformation sensor according to an exemplary embodiment of the disclosure. In the embodiment, the deformation sensor is implemented in form of a sensing circuit, where FIG. 3A is a top view of a deformation sensing circuit, FIG. 3B is a side view of the deformation sensing circuit of FIG. 3A, and FIG. 3C and FIG. 3D are top views of another deformation sensing circuit.

Referring to FIG. 3A, the deformation sensing circuit 120A includes a plurality of wires 310a-310c connected in parallel with each other and a bottom electrode 320, where the wires 310a-310c are respectively spaced apart from the bottom electrode 320 by a gap in different directions (for example, x, y, z directions), so as to generate a plurality of capacitance values between the wires 310a-310c and the bottom electrode 320, and these capacitance values are varied along with the deformation of the detected sensing portions, and such capacitance value variation may be used as a reference for generating the deformation signal.

In an embodiment, the wires 310a-310c and the bottom electrode 320 of the deformation sensing circuit 120A are disposed on different planes, and a plurality of branches of the bottom electrode 320 are respectively spaced apart from the wires 310a-310c by the gap in different directions.

In detail, referring to FIG. 3A and FIG. 3B, the wires 310a-310c present a snake-cage shape, and are disposed on a wire layer 310 located above the bottom electrode 320. The wires 310a-310c and the bottom electrode 320 are, for example, connected by an elastic dielectric material 330, and the elastic dielectric material 330 is, for example, a compressible or stretchable material. One end of each of the wires 310a-310c is coupled to a top electrode 340. The bottom electrode 320 has a plurality of branches 320a-320c, where the wire 310a and the branch 320a of the bottom electrode 320 are spaced apart by a gap d1 in the x direction; the wire 310c and the branch 320c of the bottom electrode 320 are spaced apart by a gap d2 in the y direction; and the wire 310b and the branch 320b of the bottom electrode 320 are spaced apart by a gap d3 in the z direction. Through the above gaps d1-d3, the wires 310a-310c and the bottom electrode 320 may respectively produce a capacitance value corresponding to the x direction, a capacitance value corresponding to the y direction and a capacitance value corresponding to the z direction there between.

Then, referring to FIG. 3C, a difference between the deformation sensing circuit 120B of FIG. 3C and the deformation sensing circuit 120A of FIG. 3A is that a plurality of branches of the bottom electrode 320 may extend to the wire layer 310 through vias 360, and are respectively spaced apart from the wires 310a to 310c by gaps in the x, y, and z directions. Compared to FIG. 3A, distances of the gaps between the wires 310a-310c and the bottom electrode 320 of the embodiment are shortened, so that deformation detection may be more sensitive.

Thereafter, referring to FIG. 3D, a difference between the deformation sensing circuit 120C of FIG. 3D and the deformation sensing circuit 120A of FIG. 3A is that a part of the branches of the bottom electrode 320 may extend to the wire layer 310 through vias 360, and are respectively spaced apart from the wires 310a and 310b by gaps in the x and y directions. On the other hand, regarding a branch 370 of the bottom electrode 320 close to the wire 310c, a top portion thereof is designed in an arc shape, thereby shortening the gap between the branch 370 and the wire 310c in the y direction, so that the deformation detection in the y direction is more sensitive.

According to a design requirement, positions of the above vias and a setting position of the arc branch may be adjusted freely to obtain the capacitance values in the x, y, and z directions.

When the sensing portion has a deformation, the deformation sensing circuits 120A-120C are squeezed by an external force to produce deformation. In this case, the gaps d1-d3 are varied, so that the capacitance values corresponding to the x, y and z directions are varied. In this way, the deformation sensing circuits 120A-120C generate deformation signals according to the above capacitance value variations.

In detail, the capacitance values are different, frequencies and characteristic impedances are also different and after the three wires corresponding to the capacitance values in the x, y, and z directions are connected in parallel, the individual capacitance values may be learned by changing the frequency. In this way, the deformation sensing circuits 120A-120C may perform frequency analysis on the capacitance values of the wires 310a-310c connected in parallel to obtain a corresponding relationship between the capacitance values and the impedance values of the wires 310a-310c connected in parallel.

Figure 4A:
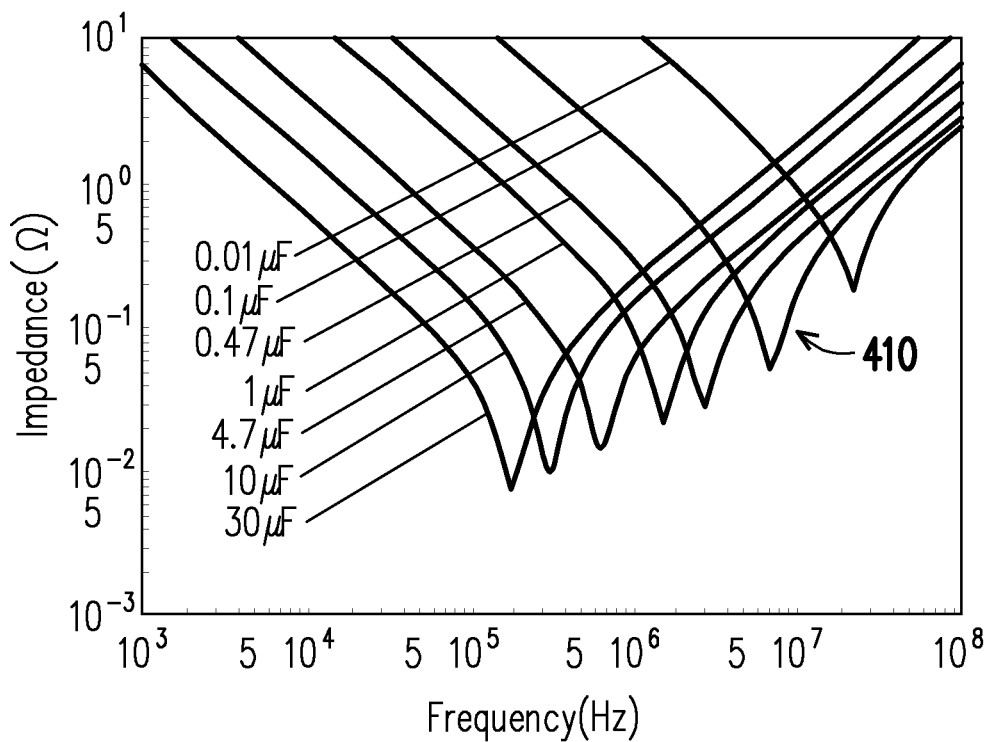
FIG. 4A and FIG. 4B are relationship charts of capacitances, frequencies and impedances of the exemplary embodiment of FIG. 3A to FIG. 3D.
Figure 4B:
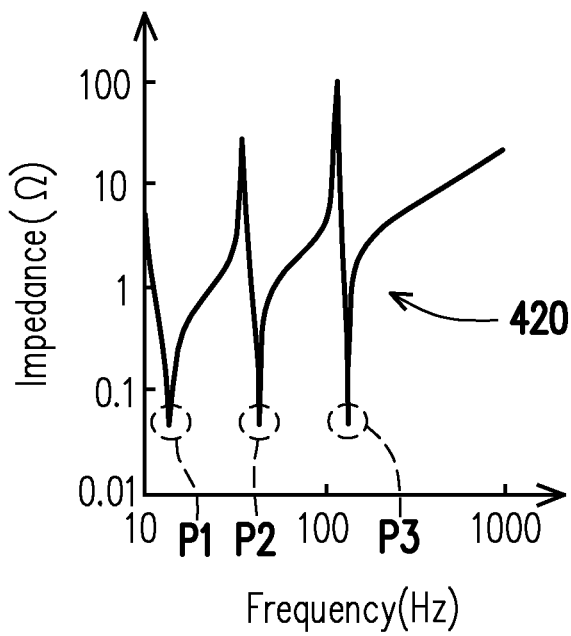

For example, FIG. 4A and FIG. 4B are relationship charts of capacitances, frequencies and impedances of the exemplary embodiment of FIG. 3A to FIG. 3D. Referring to FIG. 4A, in an impedance-frequency relationship chart of a single wire, different capacitance values (for example, 0.01 µF, 0.1 µF, 0.47 µF, etc.) correspond to different impedance-frequency relationship curves 410, and each of the relationship curves 410 presents a recognizable peak. Referring to FIG. 4B, in an impedance-frequency relationship chart of multiple parallel wires, the relationship curves corresponding to different capacitance values are merged into a relationship curve 420, and the relationship curve 420 presents a plurality of peaks (for example, three peaks P1-P3 shown in FIG. 4B), which respectively present impedance changes in different directions. Therefore, by analyzing a position of each waveform and/or peak in the relationship curve 420, the changes of the capacitance values in different directions and corresponding stress changes may be determined.

According to the above frequency analysis, the deformation sensor 120 may determine a stress change (which is, a pressure change on the deformation sensor 120 when the wrist is rotated or bent) corresponding to the change of the capacitance value of the wires 310a-310c according to the above corresponding relationship, so as to calculate a deformation amount according to the stress change, and generate the deformation signal corresponding to the deformation amount. In this way, the processing device 130 finds the compensation signal corresponding to the deformation amount in the deformation signal according to the pre-stored mapping table.

Table 1 is an example of a mapping table of deformation amounts and compensation signals, types and values of the information in the mapping table are only an example, and more complicated database information may be used to present the relationship between the deformation amounts and the compensation signals corresponding to the "deformation".

TABLE 1

| Deformation amount (percentage) | Correction level | Compensation signal |
|---|---|---|
| 0% | 1 | 0000 |
| 10% | 2 | 0001 |
| 20% | 3 | 0010 |
| 30% | 4 | 0011 |
| 40% | 5 | 0100 |
| 50% | 6 | 0110 |
| 60% | 7 | 0111 |
| 70% | 8 | 1000 |
| 80% | 9 | 1001 |
| 90% | 10 | 1010 |
| 100% | 11 | 1011 |

According to value variations in the table 1, it is learned that the larger the deformation amount of the physiological signal sensor is, the higher the correction level is, and the higher the value of the compensation signal is.

As described above, the wristband biosensing system 100 may pre-determine the position of the target portion by using the physiological signal sensors 110 arranged in an array, and select the physiological signal sensors 110 located adjacent to the target portion, and correct and output the physiological signals detected by these physiological signal sensors 110. In this way, the wristband biosensing system 100 may solve the influence on the detected signals caused by displacement of the wristband body.

Figure 5:
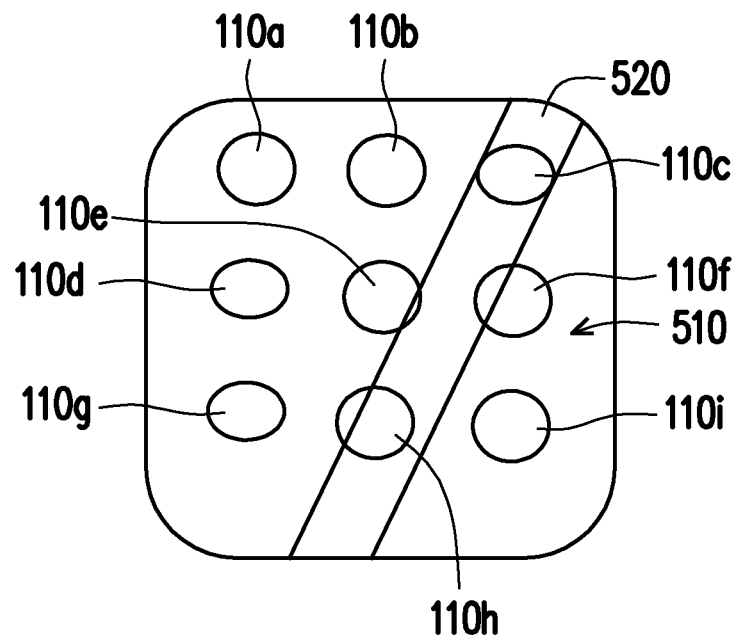
FIG. 5 is a position relationship diagram of physiological signal sensors according to an exemplary embodiment of the disclosure.

For example, FIG. 5 is a position relationship diagram of the physiological signal sensors according to an exemplary embodiment of the disclosure. Referring to FIG. 1 and FIG. 5, the physiological signal sensors 110a-110i are, for example, disposed on a wristband body 510 in an array. The processing device 130 of the wristband biosensing system 100 may compare the physiological signals detected by the physiological signal sensors 110a-110i with the referential physiological signal map of the sensing portion to select the physiological signals to be corrected and output.

In detail, the processing device 130 may compare the physiological signals detected by each of the physiological signal sensors 110a-110i with the referential physiological signal map of the wrist artery to select the physiological signal sensors 110c and 110h located at the region of the writ artery 520 (i.e. the target portion), so as to correct and output the physiological signals obtained by the physiological signal sensors 110c and 110h.

Figure 6:
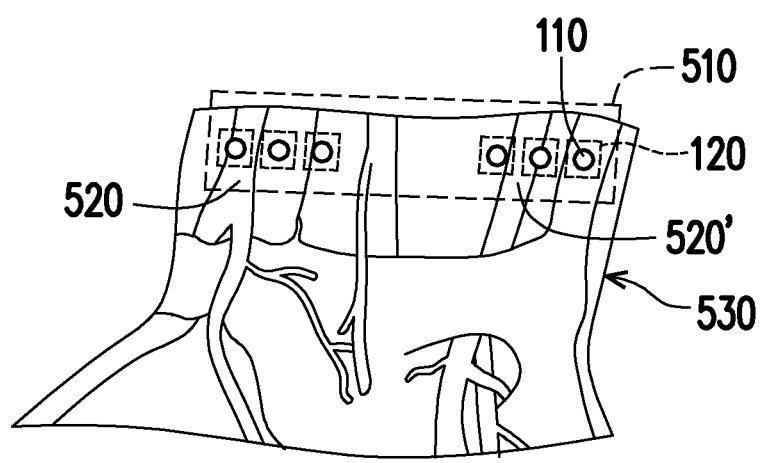
FIG. 6 is a position relationship diagram of physiological signal sensors and a wristband body according to an exemplary embodiment of the disclosure.

FIG. 6 is a position relationship diagram of the physiological signal sensors and the wristband body according to an exemplary embodiment of the disclosure. Referring to FIG. 6, the wristband body 510 is worn on the wrist 530 of the user, and the physiological signal sensors 110 may be disposed on the wristband body 510 at positions corresponding to the sensing portions of the wrist 530, i.e. positions of the wrist arteries 520 and 520', where the deformation sensors 120 may be disposed around each of the physiological signal sensors 110 (in the embodiment, the deformation sensors 120 cover the physiological signal sensors 110, and in other embodiments, the deformation sensors 120 may also be disposed at any position around the physiological signal sensors 110, which is not limited by the disclosure). In this way, the physiological signal sensors 110 may detect the physiological signals (for example, pulses or a blood pressure) of the wrist arteries 520 and 520' based on the above configuration method.

Figure 7A:
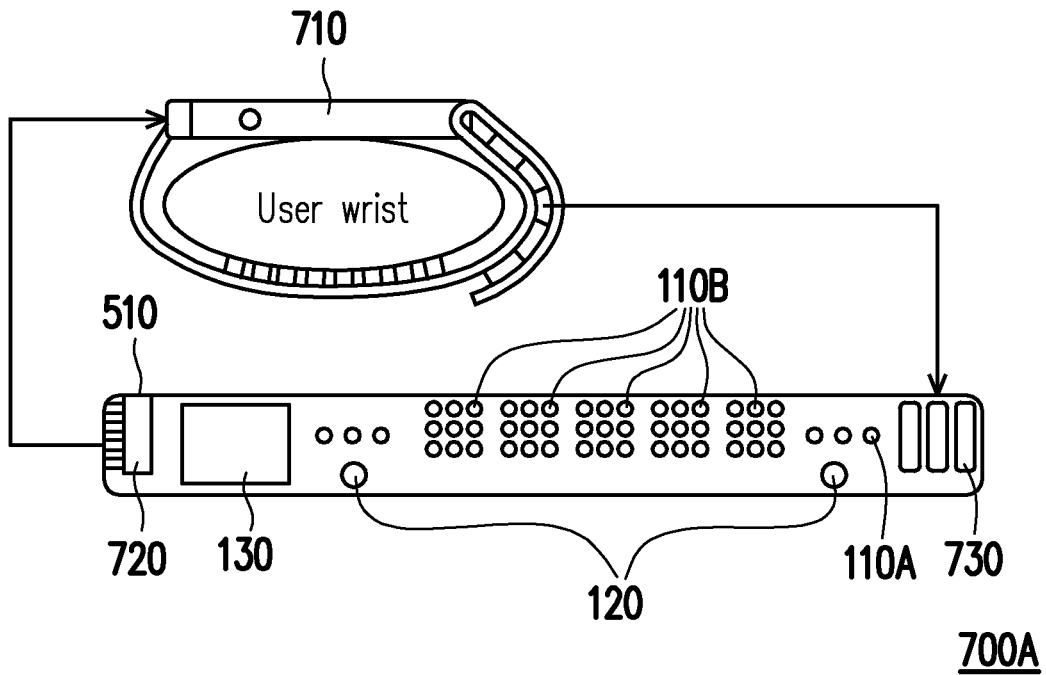
FIG. 7A and FIG. 7B are schematic diagrams of a wristband biosensing apparatus according to an exemplary embodiment of the disclosure.
Figure 7B:
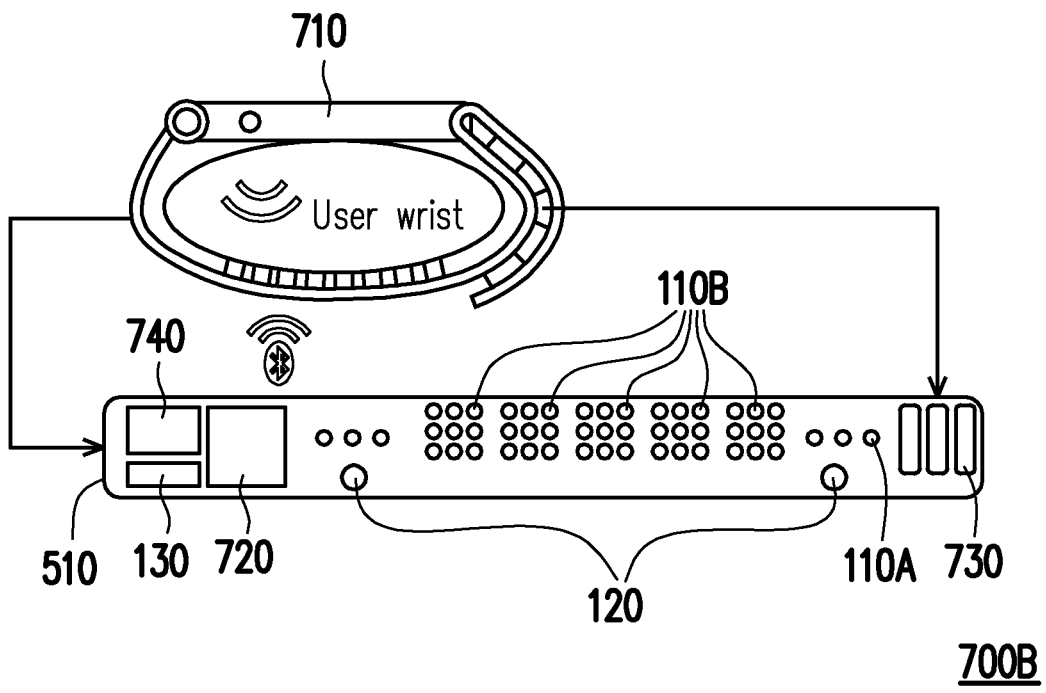

FIG. 7A and FIG. 7B are schematic diagrams of a wristband biosensing apparatus according to an exemplary embodiment of the disclosure. Referring to FIG. 7A, the wristband biosensing apparatus 700A includes a host 710, a connection device 720, a wristband body 510, physiological signal sensors 110A and 110B, deformation sensors 120 and a processing device 130. Moreover, a wristband buckle 730 may be disposed on the wristband biosensing apparatus 700A according to an actual requirement to facilitate the user to wear and adjust the tightness. The connection device 720 may be connected to the host 710. In an embodiment, the connection device 720 may be a connector, which is connected to the host 710 in a wired manner, and the host 710 may be a smart watch, a bracelet or any electronic device.

The wristband body 510 may be worn on the wrist of the user. The physiological signal sensors 110A and 110B may be disposed on the wristband body 510 at positions corresponding to the sensing portions of the wrist, so as to detect the physiological signals of each of the sensing portions. The deformation sensors 120 may be disposed around the physiological signal sensors 110A and 110B to detect deformation of each of the sensing portions, and output deformation signals. The processing device 130 may be coupled to the physiological signal sensors 110A and 110B and the deformation sensors 120 to receive the physiological signals and the deformation signals to query the compensation signals corresponding to the deformation signals, and correct the physiological signals by using the compensation signals, so as to output the corrected physiological signals of each of the sensing portions to the host 710 through the connection device 720.

In an embodiment, the physiological signal sensor 110A may be a PPG sensor, and the physiological signal sensor 110B may be a sensor for detecting each muscle group, for example, an Electromyography Sensor (EMG sensor), or a sensor for measuring an electrophysiological activity of heart, for example, an Electrocardiography Sensor (ECG sensor). In an embodiment, the connection device 720 may further receive electric power from the host 710 to supply operation of the wristband biosensing apparatus 700A.

Referring to FIG. 7B, a difference between the wristband biosensing apparatus 700B and the wristband biosensing apparatus 700A of FIG. 7A is that the connection device 720 of the wristband biosensing apparatus 700B is a communication interface supporting a wireless communication standard, and the wristband biosensing apparatus 700B further includes a battery 740 that provides the electric power required by the operation of the wristband biosensing apparatus 700B. The wireless communication standard includes Wireless Fidelity (Wi-Fi), Bluetooth, Infrared, Near-Field Communication (NFC), or Device-to-Device (D2D), which is not limited by the disclosure.

In an embodiment, similar to FIG. 3A to FIG. 3D, the deformation sensor 120 may include a plurality of wires connected in parallel and a bottom electrode, and the plurality of wires are respectively spaced apart from the bottom electrode by a gap in different directions, so as to generate a plurality of capacitance values between the wires and the bottom electrode, and these capacitance values are varied along with the deformation of the detected sensing portions, where the deformation sensor 120 may further generate the deformation signals according to a plurality of capacitance value variations.

Figure 8:
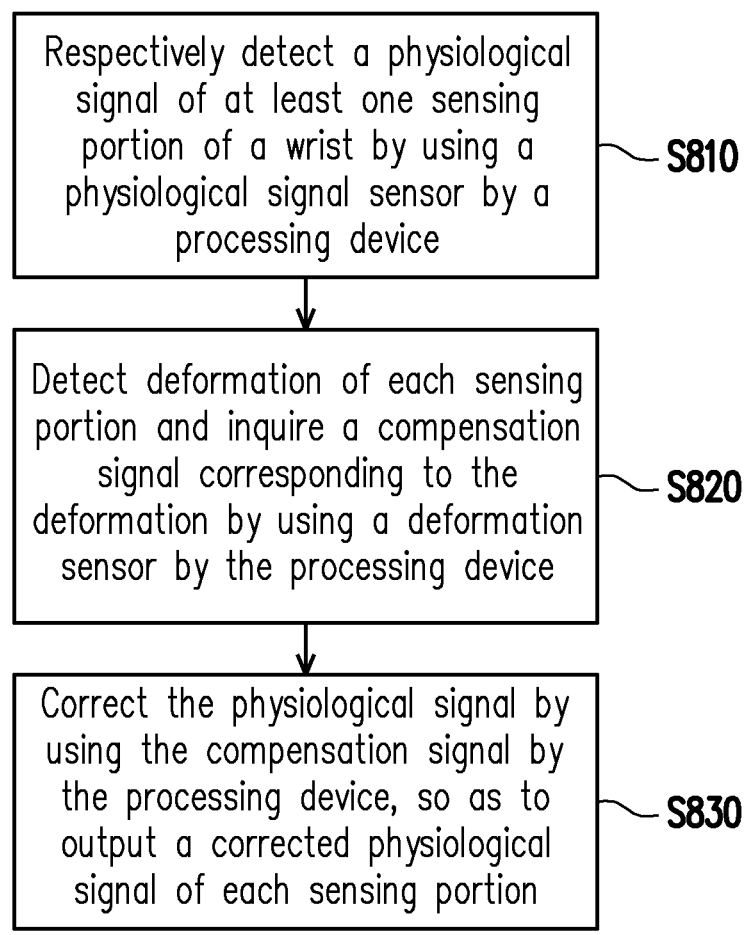
FIG. 8 is a flowchart illustrating a biosensing method according to an exemplary embodiment of the disclosure.

FIG. 8 is a flowchart illustrating a biosensing method according to an exemplary embodiment of the disclosure. The biosensing method is adapted to the wristband biosensing system 100 of the aforementioned embodiment. Referring to FIG. 1 and FIG. 8, in a step S810, the processing device 130 uses the physiological signal sensors 110 to respectively detect a physiological signal of at least one sensing portion of the wrist. The physiological signal sensors 110 are disposed on the biosensing apparatus in an array, and the processing device 130 compares the detected physiological signals with the referential physiological signal map to select the physiological signals of the sensing portions to be corrected and output. In a step S820, the processing device 130 uses the deformation sensors 120 to detect deformation of each sensing portion, and inquire a compensation signal corresponding to the deformation. In a step S830, the processing device 130 uses the compensation signal to correct the physiological signal, so as to output a corrected physiological signal of each sensing portion. The processing device 130 selects physiological signals with the highest signal map similarity, the highest intensity or both from the detected physiological signals to serve as the physiological signals of the sensing portion to be corrected and output according to the referential physiological signal map. The aforementioned embodiments may be referred for detailed implementations of the above steps.

In summary, the wristband biosensing system of the disclosure uses the compensation signals corresponding to the user wrist deformation to correct the physiological signals influenced by the user wrist deformation. In this way, the wristband biosensing system may eliminate the influence of the user wrist deformation on the physiological signals. Moreover, the wristband biosensing system may further use a physiological signal sensor array to determine the target portion to obtain the correct physiological signals. In this way, the wristband biosensing system may prevent the influence of the displacement of the wristband body on the physiological signals.

It will be apparent to those skilled in the art that various modifications and variations can be made to the disclosed embodiments without departing from the scope or spirit of the disclosure. In view of the foregoing, it is intended that the disclosure covers modifications and variations provided they fall within the scope of the following claims and their equivalents.

What is claimed is:

1. A wristband biosensing system, comprising:
a wristband body, worn on a wrist of a user;
at least one physiological signal sensor, disposed on the wristband body at a position corresponding to at least one sensing portion of the wrist, and configured to detect a physiological signal of each of the at least one sensing portion;
at least one deformation sensor, disposed around each of the at least one physiological signal sensor, and configured to detect deformation of each of the at least one sensing portion and output a deformation signal; and
a processing device, coupled to the at least one physiological signal sensor and the at least one deformation sensor, and configured to receive the physiological signal and the deformation signal, inquire a compensation signal corresponding to the deformation signal, and correct the physiological signal by using the compensation signal, so as to output a corrected physiological signal of each of the at least one sensing portion,
wherein each of the at least one deformation sensor comprises a plurality of wires connected in parallel and a bottom electrode, the plurality of wires are respectively spaced apart from the bottom electrode by a gap in different directions, so as to generate a plurality of capacitance values between the plurality of wires and the bottom electrode, and the plurality of capacitance values generate a plurality of capacitance value variations along with deformation of each of the at least one sensing portion, wherein each of the at least one deformation sensor generates the deformation signal according to the plurality of capacitance value variations.

2. The wristband biosensing system as claimed in claim 1, wherein the plurality of wires and the bottom electrode of each of the at least one deformation sensor are disposed on different planes, and a plurality of branches of the bottom electrode are respectively spaced apart from the plurality of wires by the gap in different directions.

3. The wristband biosensing system as claimed in claim 2, wherein at least one branch in the plurality of branches of the bottom electrode of each of the at least one deformation sensor extends to a plane where the plurality of wires are located through vias, and is spaced apart from one of the plurality of wires by the gap.

4. The wristband biosensing system as claimed in claim 1, wherein the at least one physiological signal sensor is disposed on the wristband body in an array, and the processing device compares the detected physiological signal with a referential physiological signal map to select a physiological signal of the at least one sensing portion to be corrected and output.

5. The wristband biosensing system as claimed in claim 4, wherein the processing device selects a physiological signal with a highest signal map similarity, a highest intensity, or both from the detected physiological signal to serve as the physiological signal of the at least one sensing portion to be corrected and output.

6. The wristband biosensing system as claimed in claim 1, wherein the at least one deformation sensor is disposed around the at least one physiological signal sensor in a one-to-one manner or a many-to-one manner.

7. The wristband biosensing system as claimed in claim 1, wherein the at least one physiological signal sensor is a photoplethysmography sensor.

8. The wristband biosensing system as claimed in claim 1, further comprising:
a display device, connected to the processing device in a wired or wireless manner, and displaying the corrected physiological signal of each of the at least one sensing portion output by the processing device.

9. A biosensing method, adapted to a biosensing apparatus worn on a wrist of a user, the biosensing apparatus comprising at least one physiological signal sensor, at least one deformation sensor, and a processing device, each of the at least one deformation sensor comprising a plurality of wires connected in parallel and a bottom electrode, the plurality of wires being respectively spaced apart from the bottom electrode by a gap in different directions, the biosensing method comprising:
respectively detecting a physiological signal of at least one sensing portion of the wrist by using the at least one physiological signal sensor by the processing device;
detecting deformation of each of the at least one sensing portion by detecting a plurality of capacitance value variations of a plurality of capacitance values between the plurality of wires and the bottom electrode along with deformation of each of the at least one sensing portion and generating a deformation signal according to the plurality of capacitance value variations, and inquiring a compensation signal corresponding to the deformation signal by the processing device; and
correcting the physiological signal by using the compensation signal by the processing device, so as to output a corrected physiological signal of each of the at least one sensing portion.

10. The biosensing method as claimed in claim 9, wherein the at least one physiological signal sensor is disposed on the biosensing apparatus in an array, and the processing device compares the detected physiological signal with a referential physiological signal map to select a physiological signal of the at least one sensing portion to be corrected and output.

11. The biosensing method as claimed in claim 10, wherein the processing device selects a physiological signal with a highest signal map similarity, a highest intensity, or both from the detected physiological signal to serve as the physiological signal of the at least one sensing portion to be corrected and output.

12. A wristband biosensing apparatus, comprising:
a connection device, connected to a host;
a wristband body, worn on a wrist of a user;
at least one physiological signal sensor, disposed on the wristband body at a position corresponding to at least one sensing portion of the wrist, and configured to detect a physiological signal of each of the at least one sensing portion;
at least one deformation sensor, disposed around each of the at least one physiological signal sensor, and configured to detect deformation of each of the at least one sensing portion and output a deformation signal; and
a processing device, coupled to the at least one physiological signal sensor and the at least one deformation sensor, and configured to receive the physiological signal and the deformation signal, inquire a compensation signal corresponding to the deformation signal, and correct the physiological signal by using the compensation signal, so as to output a corrected physiological signal of each of the at least one sensing portion to the host,
wherein each of the at least one deformation sensor comprises a plurality of wires connected in parallel and a bottom electrode, the plurality of wires are respectively spaced apart from the bottom electrode by a gap in different directions, so as to generate a plurality of capacitance values between the plurality of wires and the bottom electrode, and the plurality of capacitance values generate a plurality of capacitance value variations along with deformation of each of the at least one sensing portion, wherein each of the at least one deformation sensor generates the deformation signal according to the plurality of capacitance value variations.

13. The wristband biosensing apparatus as claimed in claim 12, wherein the connection device comprises a connector or a communication interface supporting a wireless communication standard, and the wireless communication standard comprises Wireless Fidelity, Bluetooth, infrared, near-field communication, or device-to-device.

14. The wristband biosensing apparatus as claimed in claim 12, wherein the connection device is further configured to receive electric power from the host to supply an operation of the wristband biosensing apparatus.

15. The wristband biosensing apparatus as claimed in claim 12, further comprising a battery that provides electric power required by an operation of the wristband biosensing apparatus.

* * * * *